(12) United States Patent  
Rushbrooke et al.

(10) Patent No.: US 6,961,125 B2  
(45) Date of Patent: Nov. 1, 2005

(54) LUMINESCENCE IMAGER

(75) Inventors: John Gordon Rushbrooke, Newport Beach, CA (US); Claire Elizabeth Hooper, Newport Beach, CA (US)

(73) Assignee: Packard Instrument Company, Inc., Meriden, CT (US)

( * ) Notice: Subject to any disclaimer, the term of this patent is extended or adjusted under 35 U.S.C. 154(b) by 0 days.

(21) Appl. No.: 10/250,956

(22) PCT Filed: Dec. 18, 2001

(86) PCT No.: PCT/GB01/05585

§ 371 (c)(1),  
(2), (4) Date: Jul. 3, 2003

(87) PCT Pub. No.: WO02/054049

PCT Pub. Date: Jul. 11, 2002

(65) Prior Publication Data

US 2004/0051031 A1 Mar. 18, 2004

(30) Foreign Application Priority Data

Jan. 3, 2001 (GB) .............................. 0100043

(51) Int. Cl.⁷ .............................................. G01N 21/25  
(52) U.S. Cl. ...................................... 356/417; 356/416  
(58) Field of Search ................................ 356/416–419, 356/436, 440, 246, 316–318; 250/458.1, 459.1, 461.1, 461.2

(56) References Cited

U.S. PATENT DOCUMENTS

| 4,805,461 A | * | 2/1989 | Gupta et al. .................. 73/800 |
| 6,043,880 A | * | 3/2000 | Andrews et al. ............ 356/311 |
| 6,571,118 B1 | | 5/2003 | Utzinger et al. |
| 6,608,671 B2 | * | 8/2003 | Tsien et al. .................. 356/72 |
| 2002/0039728 A1 | * | 4/2002 | Kain et al. .................... 435/6 |

FOREIGN PATENT DOCUMENTS

| EP | 0335725 A3 | 10/1989 |
| EP | 0909947 A3 | 4/1999 |
| GB | 2196734 A | 5/1988 |

* cited by examiner

Primary Examiner—Zandra V. Smith  
(74) Attorney, Agent, or Firm—Barnes & Thornburg

(57) ABSTRACT

A fiber optic epi-fluorescence imaging system in which the optical fibers are rearranged so that the system can be used for measuring luminescence samples. The system comprises at least two optical fibers (32, 46) or bundles of fibers which lead to a CCD camera (74), the fibers or bundles of fibers from all samples being arranged in two sets, a first set which are formed from a non-fluorescing material and a second set which are formed from a material which may fluoresce but enables the fibers formed therefrom to have a higher numerical aperture than those of the first set.

16 Claims, 10 Drawing Sheets

96 holes
spacing - 3.9mm
in circle - 75mm diameter 192 holes diameter - 2.0mm
spacing - 1.9mm
within 27 x 27mm
area of camera 400 - 384 = 16 , so delete 4 holes from each corner 384 holes diameter 2.0mm
Spacing 4.0mm
within 78 x 78 mm area of camera

LUMINESCENCE IMAGER

FIELD OF INVENTION

This invention concerns luminescence imaging methods and apparatus, particularly methods and apparatus which employ optical fibres and a CCD to inspect and monitor luminescence from arrays such as microtitre plates.

BACKGROUND

Reference is made to Patent Specifications GB 2339900 (and corresponding PCT specification WO 00/05569), GB 2339901, and GB 23515555, whose disclosures are herein incorporated by reference, which describe an epifluorescence imaging system designed to measure the flourescence emitted from the bottom of an array of samples when they are irradiated from beneath by excitation light. FIG. 1, taken from these Applications, shows the use of an array of typically 8×12 trifurcated fibre optic bundles arrayed in a presentation plate on which the sample plate is placed. One sub-set of fibres within a bundle is used to bring in the excitation light, and two other sub-sets of fibres in each bundle collect emitted fluorescent light into two separate filter channels to enable simultaneous measurement of dual wavelengths. After the filters the light is transmitted through single fibres, 2×96 of them, to a fibre optic input face of a CCD camera. The arrangement of optical fibre bundles at the filters is shown in FIG. 2, and of the optical fibres at the input to the CCD camera is show in FIG. 3. FIG. 4 shows how the different categories of fibres are arranged in a hexagonal pattern within a bundle.

Typically an image can be taken every second, and repeated at approximately one-second intervals.

This system has proved to be an efficient, highly sensitive measurer of fluorescence in dual wavelengths, and the ability to measure dual wavelengths simultaneously is of great value for certain assays, such as FRET assays, where a change in the ratio of the signal strengths in the two wavelengths is an indicator of chemical binding or some other attribute of the assay.

This 96-channel system can be used to measure 96-well microtitre plates, or by stepping the microtitre plate over the presentation plate, larger assay presentations such as 384, 864, 1536, 3465 . . . , well plates (i.e. having and $n^2*96$ pattern, where n is an integer).

This system is not optimised for the measurement of luminescence for which no excitation is needed, and in which a sample emits light by virtue of a chemical reaction occurring when reagents are interacting in the sample well.

Thus, for fluorescence, the fibre bundle is stood off below the well since light has to illuminate the sample evenly and receive fluorescence light with uniform efficiency from all parts of the well. This still applies even if the sample is a cellular layer on the base of the well.

Therefore although this epi-fluorescence system can be used to measure luminescence, it is not optimal, and is generally sensitive enough only for the brightest types of samples and assays. Examples of such assays include detection using luciferase enzyme; calcium detection, for example in cells, linked to the enzyme aequorin, which produces a flash of light during the reaction; and alkaline phosphatase linked assays using enhanced chemiluminescence substrates.

SUMMARY OF THE INVENTION

According to one aspect of the present invention an imaging system such as has been proposed for use with epi-fluorescence may be adapted for use with luminescence samples (which in general produce less light than epi-fluorescence samples) by optimising the position and type of fibre optic read out.

In one embodiment of the invention it is proposed to use a second presentation plate in which, say, 8×12 single fibres are mounted, each with its face immediately below or in contact with the base of the sample plate. The end face of each fibre which is to view the plate is preferably polished. Typically the fibres are optical fibres of plastics fibre material, say 2 mm diameter, which is available at low cost with relatively high numerical aperture (NA)—e.g. NA=0.5. This is to be compared with the NA (typically about 0.2) of the silica fibres which are commonly used to make the fibre bundles for an epifluorescence system. Silica fibre material is used to minimise the auto-fluorescence background that can occur in the presence of excitation light. The use of plastics material for fibres in fluorescence systems is ruled out since plastics materials tend to fluoresce.

Using such an arrangement of plastics fibres, a factor of light gathering improvement of the order of 10–20 has been obtained for luminescence samples when compared with the measurement of these samples using an epi-fluorescence system. This factor results both from the closer placing of the end of each fibre to the sample, and from the higher NA of the fibre. This makes possible the measurement of weaker types of luminescence.

According to a second aspect of the invention an epi-fluorescence imaging system may be adapted for use with luminescence samples by leading a second set of high NA fibres to the input of the CCD to which the fibres employed for epi-fluorescence samples are also led, the two sets of fibres being arranged interstitially, so that a second CCD camera is not needed.

Although the combined system will be used either for fluorescence or for luminescence, there is no risk of cross talk between the closely spaced fibres, since only one set at a time is illuminated.

According to a further aspect of the invention the luminescence light can be analysed in two wavelengths simultaneously by means of a bifurcation of each of the fibres employed when looking for luminescence. Thereafter there would be two parallel filter channels, and the two sets of fibres would be mounted interstitially to the two sets of fluorescence transfer fibres.

Certain types of luminescence assays benefit from analysis at two wavelengths. Examples of this include multi-labelled assay systems, where more than one label has been used in an assay. A further example is resonant energy transfer type assays, where a donor molecule emits light at one wavelength and a receptor molecule emits light at a second wavelength. The degree of energy transfer between the two molecules is measured by the ratio of the intensity of the two wavelengths emitted by the molecules.

The analysis algorithms already proposed (such as referred to in the Patent Specifications listed earlier) for performing measurements on fluorescence derived signals can be readily extended to luminescence signals from the CCD camera. Thus for example in the case of a 96-fibre array, a set of geometrically fixed 96 spots of light (or 2×96 spots) can be registered at a fixed displacement on the CCD from the 2×96 fluorescence spots.

A fixed array of fibres mounted in a presentation plate for luminescence measurements can be used independently of the epifluorescence system. An example would be a 16×24 fibre array to measure 384 channels simultaneously.

The fibres in the filter region may be arranged on a 100 mm-diameter filter and the system would require its own CCD camera, but this would be the only significant additional element.

The 384 fibres at the input to the CCD camera may be re-arranged if required to accommodate the aspect ratio of the CCD.

Such an arrangement can also measure a 1536 well, plate by means of a 2×2 stepping of the sample plate relative to the presentation plate.

As before, each fibre can be bifurcated to enable dual wavelength analysis. This system represents a low-cost, optically efficient means of measuring luminescence in larger size well plates, (384, 1536 wells or more).

In an arrangement embodying the invention for luminescence samples, a fixed fibre array for the measurement of arrays of samples has the following advantages over a lens based method.

(1) absence of parallax (so that wells in the corners of a plate are measured as efficiently as those in the centre of the plate) which is only avoided by using an (expensive) telecentric lens;
(2) no vignetting;
(3) no need to focus;
(4) there is much more efficient light gathering than from a lens.

Thus an optical fibre placed immediately under a well of about the same diameter has optical efficiency approximately equal to the $(NA)^2=(0.5)^2=0.25$. On the other hand a quality telecentric lens (say F=1) imaging a whole plate (size 110×75 mm) onto a CCD (size 25×25 mm) so that the lens demagnification is m=110/25=4.4, has optical efficiency $1/\{2F(1+m)\}^2=0.0086$.

A set of optical fibres as proposed is therefore about 30 times more efficient, and much less expensive than a quality lens.

The advantages of the invention are achieved if the end of each fibre that is to collect light from a sample is very close to, if not touching, the sample, either above or below the sample, such as a well in a multi-well plate, for example.

The invention also lies in a system for inspecting light emitting samples such as are contained in a well plate from each of which at least two optical fibres or bundles of fibres lead to a CCD camera, the fibres or bundles of fibres from all samples being arranged in two sets, a first set which are formed from a non-fluorescing material and a second set which are formed from a material which may fluoresce but enables the fibres formed therefrom to have a higher numerical aperture than those of the first set, one of the said at least two fibres linked to each sample belonging to the one set, and the other to the other set, wherein the fibres are arranged interstitially at the input to the camera, the light emitted from each fibre falling on a uniquely addressable region of the CCD, and the addressing of the CCD is arranged so that the addresses associated with one set of fibres, or the other, are read out and refreshed to produce an output signal for analysis.

By reading out the addresses relating to the first set of fibres, an output signal is obtained relating to any fluorescence from the samples.

By reading out the addresses relating to the second set of fibres an output signal will relate to any luminescence produced by the samples.

Where the samples need to be excited so as to produce fluorescence, additional fibres lead to the samples from an excitation source.

Additional sets of fibres, each set illuminating a different unique set of addresses of the CCD, may be provided with appropriate wavelength selection as by filtering, to enable dual wavelength analysis to be performed on light emitting samples.

Using bi-furcated fibres in the second set, so as to produce 2N fibres leading from N wells, with one set of N leading to the CCD input, may allow the other set to be used for transmitting excitation radiation from a suitable source to the samples, thereby obviating the need for a third set of N fibres to the wells, for conveying excitation radiation thereto.

Figure 5:
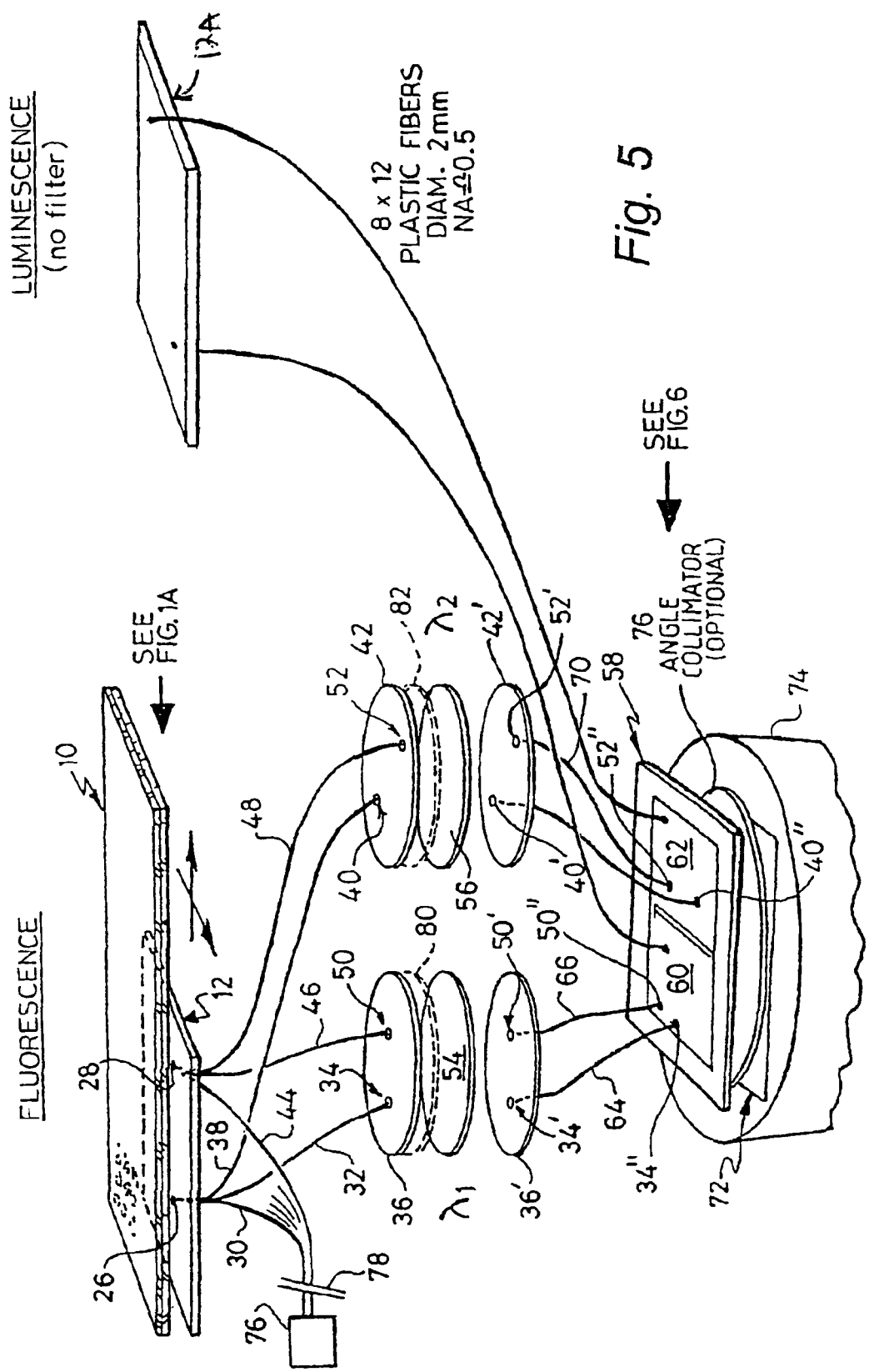
FIG. 5 shows in perspective an arrangement similar to FIG. 1, but with both flouresence and luminescence measurement in accordance with the invention.

The invention is illustrated by way of example in FIGS. 5 onwards.

The sample plate 10 is shown over a first presentation plate 12 for measuring fluorescence. The invention extends to current epi-flourescence system into a whole new application, namely detection of luminescence, at a minimal cost, and in a technically simple manner. As before, microtitre sample plates having 384, 864, 1536 . . . wells, based on a 96-channel pattern, can be measured by stepping the sample plate 10 over a second presentation plate 12A. FIG. 5 shows a 96-channel luminescence reading head. The presentation plates 12 and 12A are smaller in area than the sample plate 10.

Figure 6:
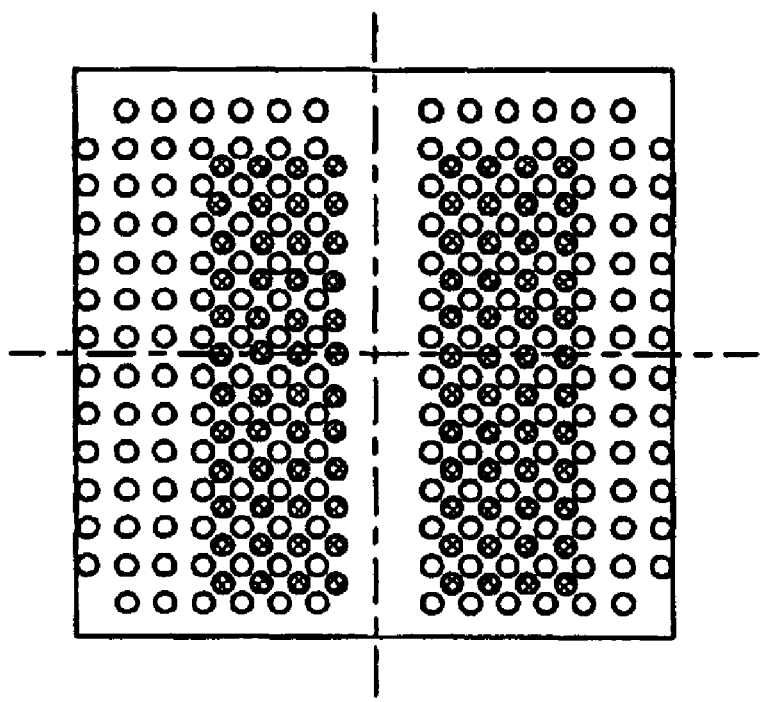
FIG. 6 shows an arrangement of extra fibres at the CCD camera.
Figure 7:
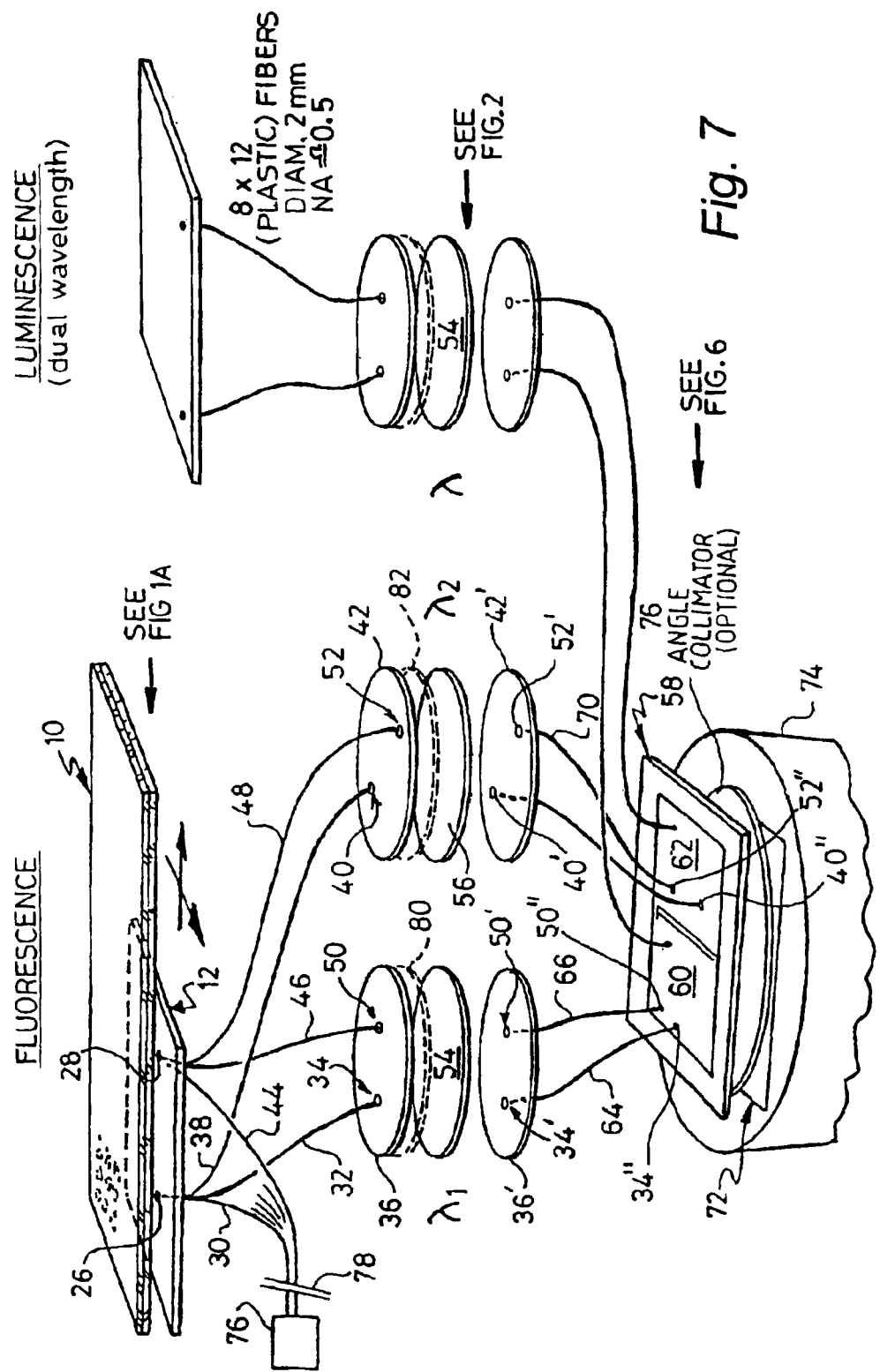
FIG. 7 is a view similar to FIG. 5, but with a filter in the luminescence system.

A filter can be added to this luminescence system, as shown in FIG. 7, which needs the same arrangement of 96 extra fibres at the CCD shown in FIG. 6.

Figure 1A:
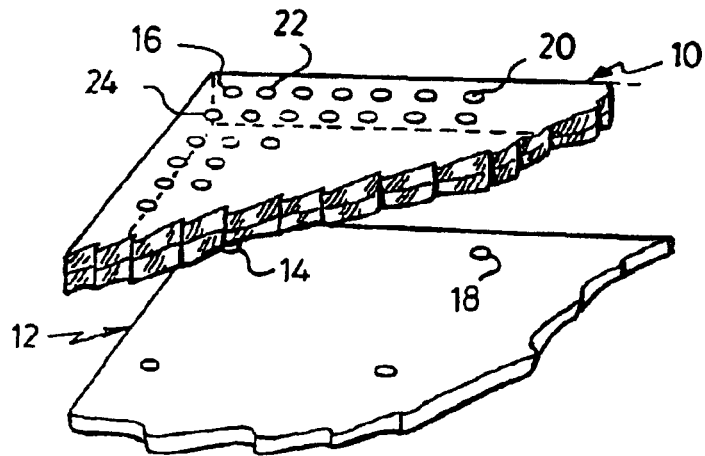
FIGS. 1 and 1A together schematically illustrate in perspective an array of fibre optic bundles with a presentation plate on which a sample plate is placed.
Figure 1:
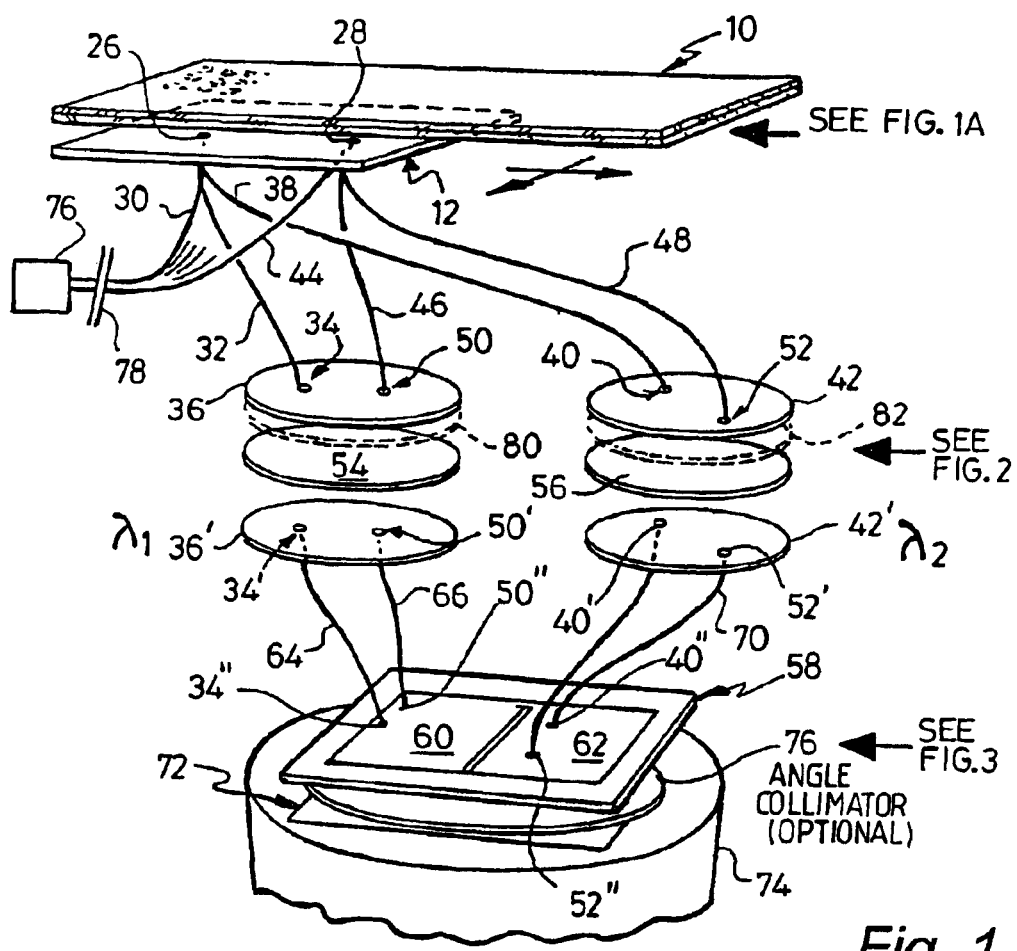
Figure 2:
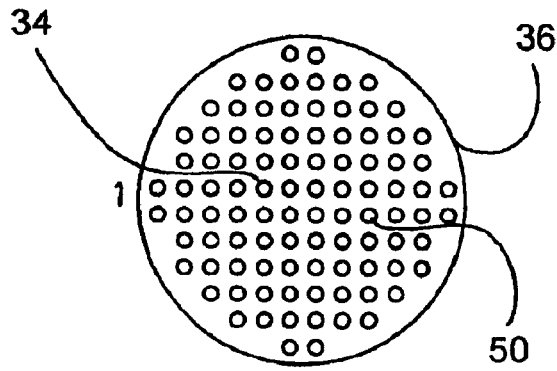
FIGS. 2 and 3 show an arrangement of a fibre bundle at a filter and at a CCD camera, respectively.
Figure 3:
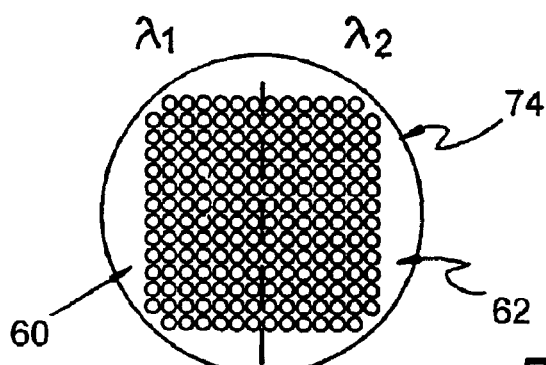
Figure 4:
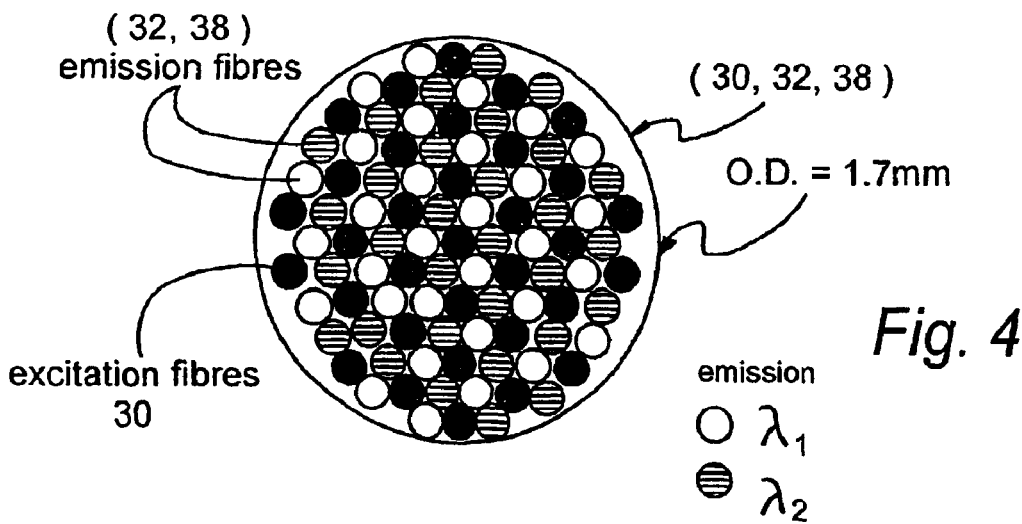
FIG. 4 shows the arrangement of different filters in a hexagonal pattern.

The arrangement of fibres in the filter space would be as in FIG. 2. As with the fluorescence version, there is a rearrangement of the fibres from the sample presentation plate to the filter space, if a filter is used, and again to the input to the CCD camera. Note that the filter space does not necessarily need to be as thick as in the fluorescence version, as there is no excitation light that has to be blocked from entering the emission path, allowing simpler, thinner filters to be used for the luminescence filter space.

FIG. 6 shows the interstitial arrangement of the fibres to be used for transmitting luminescence light to the camera, with those of the known epi-fluorescence system. All the fibres lead to the one entrance to the CCD camera.

Figure 8:
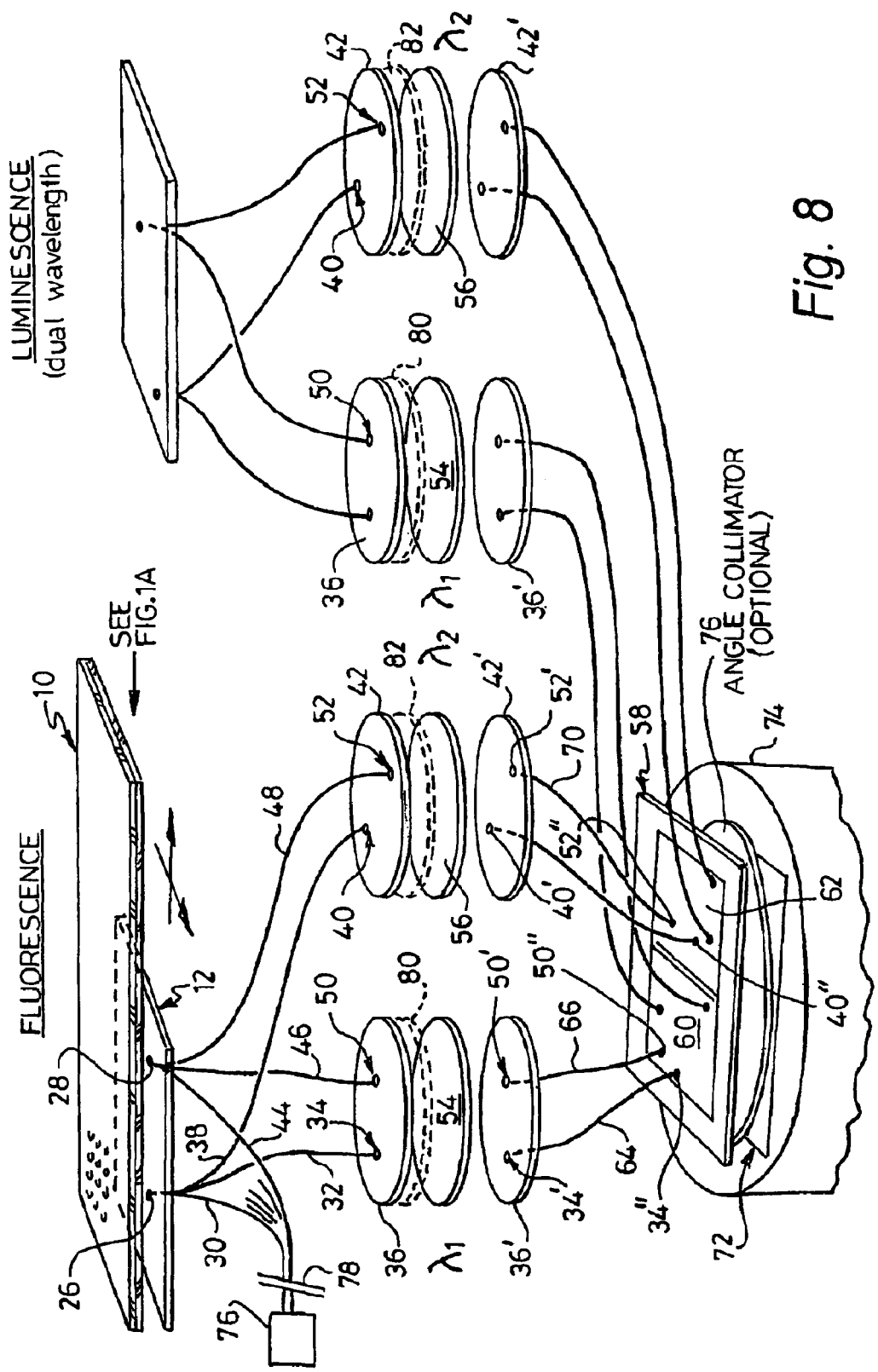
FIG. 8 is a modification of FIG. 7 with bifurcation of the luminescence fibres.

Bifurcation of the luminescence fibres is shown in FIG. 8.

Figure 9:
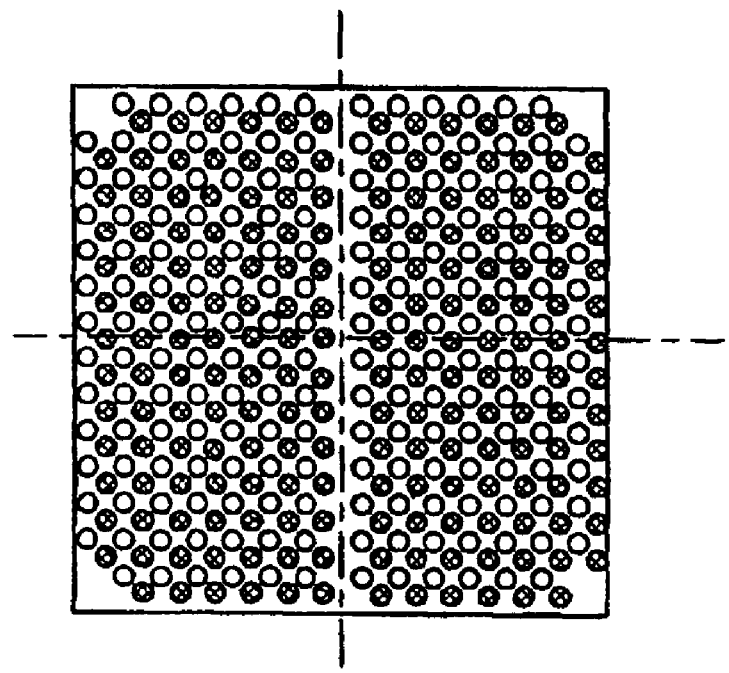
FIG. 9 shows the two sets of fibres with interstitial placement.

Interstitial placement of the two sets of fibres is again shown in FIG. 9.

Figure 10:
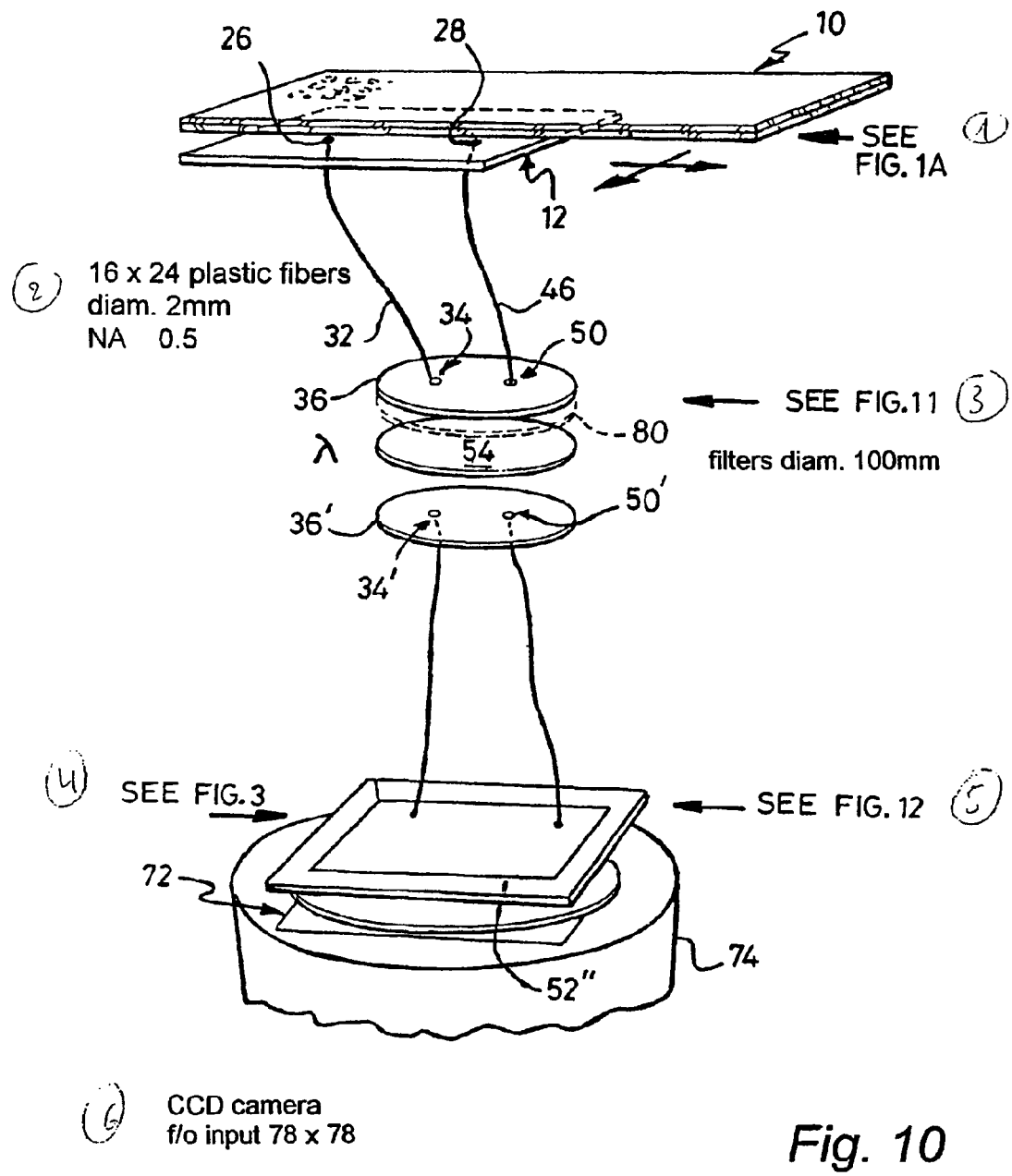
FIG. 10 shows how all the wells of a 384 well plate can be simultaneously inspected.
Figure 11:
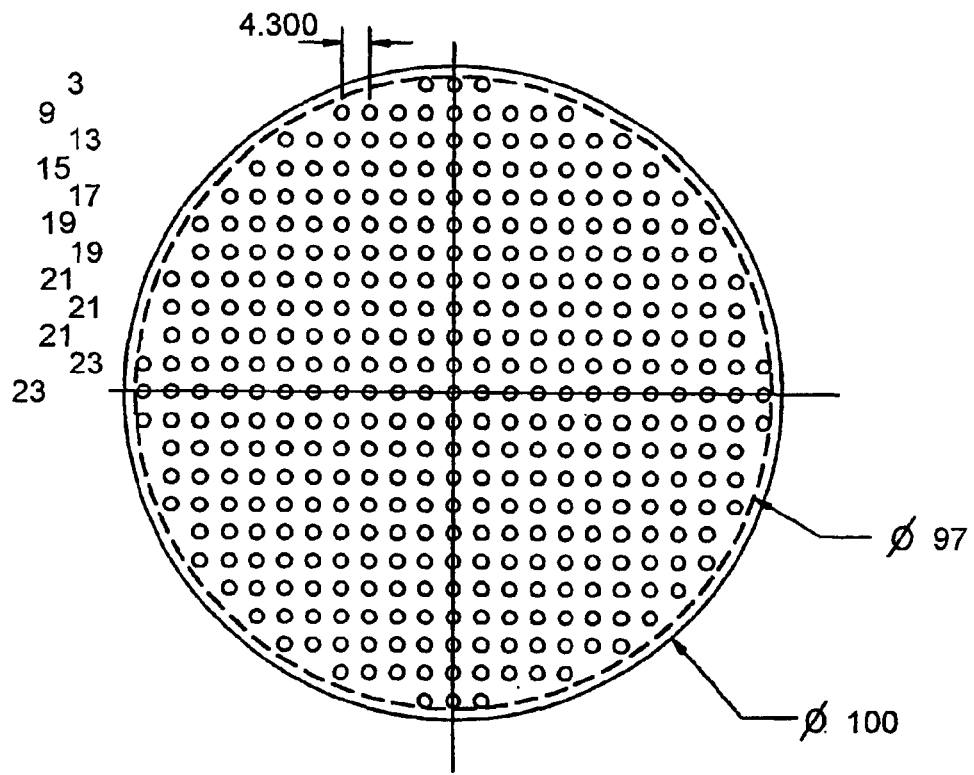
FIGS. 11 and 12 show an arrangement respectively of fibres in the epiflourescence system and at the CCD camera.

FIG. 10 shows an example of a 16×24 fibre array, which allows for simultaneous inspection of all the wells in a 384 well plate. As shown in FIG. 11, the 384 fibres are arranged on a 100 mm diameter filter where they extend through the filter space of the epi-fluorescence system.

Figure 12:
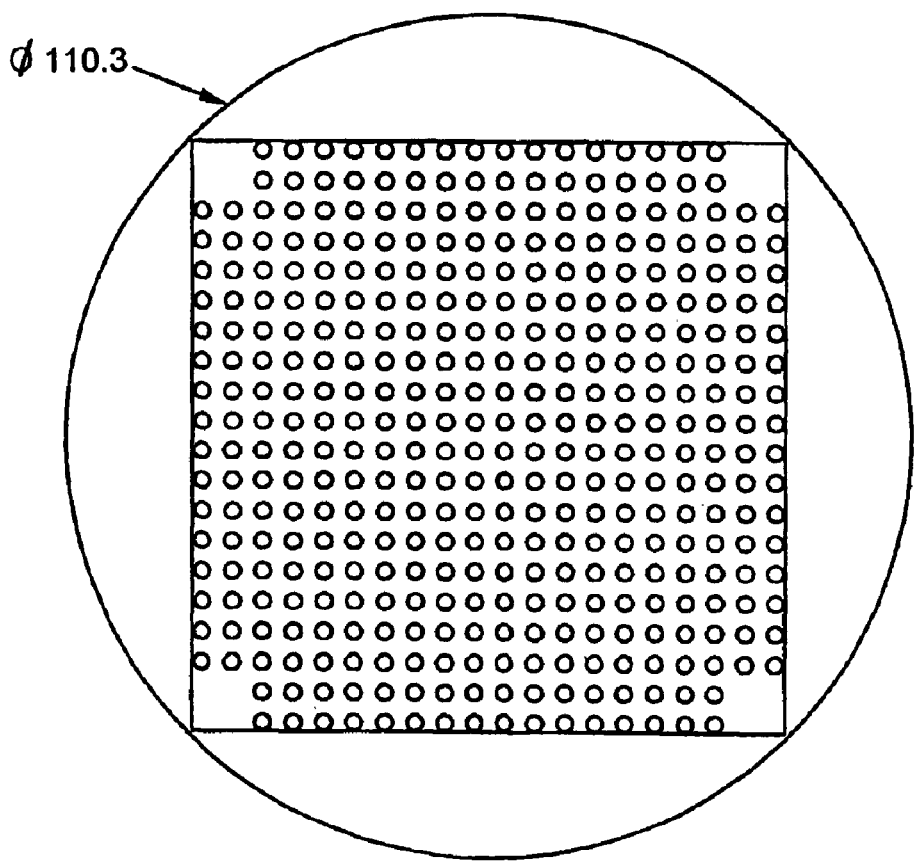

FIG. 12 shows the arrangement of the 384 fibres at the CCD camera input.

What is claimed is:

1. A system for alternatively measuring epi-fluorescence or luminescence produced by samples in a sample plate, comprising a first presentation plate for measuring epifluorescence and having an array of silica optical fibres of numerical aperture (NA) of the order of 0.2 for presenting to at least some of the samples in the sample plate at a small spacing therefrom to convey epi-fluorescence from the samples to a CCD camera, and a second presentation plate for measuring luminescence and located immediately adjacent to or in contact with the sample plate, the second presentation plate presenting the ends of a matching array of optical fibres to at least part of the array of samples, each such fibre having an NA greater than 0.2, and the said array of optical fibres from the second plate conveying luminescence emitted by the samples to a CCD camera.

2. A system according to claim 1, wherein the optical fibres associated with the second presentation plate have an NA of about 0.5.

3. A system according to claim 1, wherein the optical fibres associated with the second presentation plate are made of plastics material.

4. A system according to claim 1, wherein the ends of the optical fibres associated with the second presentation plate and viewing the sample plate, are polished.

5. A system according to claim 1, wherein, at the CCD camera, the fibres for conveying epi-fluorescence are arranged interstitially with the fibres for conveying luminescence, and all the fibres are led to a single CCD camera so that a second CCD camera is not required, and wherein an excitation source for epi-flouresence measurements is switched off during luminescence measurements.

6. A system according to claim 1, wherein the fibres for conveying luminescence are bifurcated to enable the luminescence to be conveyed to the CCD camera by the fibre subsets including two parallel filter channels.

7. A system according to claim 6, wherein the fibres for conveying epi-flouresence are also arranged in subsets including two filter channels, and the two luminescence subsets are mounted interstitially to the two epi-fluorescence subsets.

8. A system according to claim 1, wherein the fibres are re-arranged at the CCD camera to accommodate the aspect ratio of the camera.

9. A system according to claim 1, wherein an analysis algorithm is employed to measure the luminescence signals received at the CCD camera, said algorithm being a modification of a known algorithm for measuring epi-flouresence signals.

10. A system according to claim 1, wherein said first presentation plate has an area smaller than the area of the sample plate, and the sample plate and the first presentation plate are relatively movable to enable luminescence from different groups of samples to be measured in succession.

11. A system according to claim 1, wherein said second presentation plate has an area smaller than the area of the sample plate and the latter and the second presentation plate are relatively movable to enable epi-fluorescence from different groups of samples to be measured in succession.

12. A system for inspecting light emitting samples such as are contained in a well plate from each of which at least two optical fibres or bundles of fibres lead to a CCD camera, the fibres or bundles of fibres from all samples being arranged in two sets, a first set which are formed from a non-fluorescing material and a second set which are formed from a material which may fluoresce but enables the fibres formed therefrom to have a higher numerical aperture than those of the first set, one of the said at least two fibres linked to each sample belonging to the one set, and the other to the other set, wherein the fibres are arranged interstitially at the input to the CCD camera, and the addressing of the CCD is arranged so that the addresses associated with one set of fibres, or the other, are read out and refreshed to produce an output signal for analysis.

13. A system according to claim 12, wherein, by reading out the addresses relating to the first set of fibres, an output signal is obtained relating to any fluorescence from the samples, and by reading out the addresses relating to the second set of fibres an output signal is obtained relating to any luminescence produced by the samples.

14. A system according to claim 12, wherein, when the samples need to be excited so as to produce fluorescence, additional fibres lead to the samples from an excitation source.

15. A system according to claim 12, wherein additional sets of fibres, each set illuminating a different unique set of addresses of the CCD, may be provided with appropriate wavelength selection as by filtering, to enable dual wavelength analysis to be performed on light emitting samples.

16. A system according to claim 12, wherein bi-furcated fibres are used in the second set, so as to produce 2N fibres leading from N wells, with one set of N leading to the CCD input, and the first set is used for transmitting excitation radiation from a suitable source to the samples.

* * * * *